(12) United States Patent
Gozum

(10) Patent No.: US 9,310,310 B2
(45) Date of Patent: Apr. 12, 2016

(54) FLOWABLE DRY POWDER COMPOSITION

(75) Inventor: John E. Gozum, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 273 days.

(21) Appl. No.: 13/534,030

(22) Filed: Jun. 27, 2012

(65) Prior Publication Data

US 2013/0052743 A1    Feb. 28, 2013

Related U.S. Application Data

(60) Provisional application No. 61/527,934, filed on Aug. 26, 2011.

(51) Int. Cl.
  *G01N 21/78* (2006.01)
  *G01N 31/22* (2006.01)

(52) U.S. Cl.
  CPC ............ *G01N 21/78* (2013.01); *G01N 31/22* (2013.01)

(58) Field of Classification Search
  CPC ... G01N 21/78; G01N 31/22; G01N 33/1813; G01N 21/29; G01N 33/84; G01N 21/25; G01N 21/77; G01N 33/20; C07D 213/72; C07D 15/0026

USPC ..................................................... 436/83, 73
  See application file for complete search history.

(56) References Cited

U.S. PATENT DOCUMENTS

| | | |
|---|---|---|
| 5,039,618 A | 8/1991 | Stone |
| 5,550,061 A | 8/1996 | Stone |
| 2009/0286323 A1 | 11/2009 | Yamamoto |
| 2011/0008898 A1 | 1/2011 | Yamauchi |

FOREIGN PATENT DOCUMENTS

| | | |
|---|---|---|
| EP | 2 259 056 | 12/2010 |
| JP | 2007-298320 | 11/2007 |
| JP | 2007/327886 | 12/2007 |
| WO | 2004-057312 | 7/2004 |

OTHER PUBLICATIONS

3M Glass Bubbles K Series, S Series, 2009, 3M Oil and Gas, 4 pages.
International Search Report, PCT/US2012/050760, mailed Dec. 14, 2012, 3 pages.

*Primary Examiner* — Lyle Alexander
*Assistant Examiner* — Dwan A Gerido
(74) *Attorney, Agent, or Firm* — Kenneth B. Wood

(57) ABSTRACT

A flowable dry powder composition comprising a mixture of diphenylcarbazide particles and glass bubbles; kits containing such compositions; methods of filling containers with such compositions; and, methods of using such compositions in the detecting of hexavalent chromium.

18 Claims, 1 Drawing Sheet

_US 9,310,310 B2_

FLOWABLE DRY POWDER COMPOSITION

CROSS REFERENCE TO RELATED APPLICATION

This application claims the benefit of U.S. Provisional Patent Application No. 61/527,934, filed Aug. 26, 2011, the disclosure of which is incorporated by reference herein in its entirety.

BACKGROUND

Diphenylcarbazide is often used as an indicator for the detection, e.g. colorimetric detection, of hexavalent chromium.

SUMMARY

Disclosed herein are: a flowable dry powder composition comprising a mixture of diphenylcarbazide particles and glass bubbles; kits containing such compositions; methods of filling containers with such compositions; and, methods of using such compositions in the detecting of hexavalent chromium.

Thus in one aspect, herein is disclosed a flowable dry powder composition comprising a mixture of diphenylcarbazide particles and glass bubbles.

Thus in another aspect, herein is disclosed a kit for detecting hexavalent chromium, comprising at least one disposable swab comprising a secondary container that contains: a breakable container containing a flowable dry powder composition comprising a mixture of diphenylcarbazide particles and glass bubbles, and, a buffer solution.

Thus in another aspect, herein is disclosed a method of filling a container with a flowable dry powder composition, the method comprising flowing a flowable dry powder composition comprising a mixture of diphenylcarbazide particles and glass bubbles into the container.

Thus in still another aspect, herein is disclosed a method of detecting hexavalent chromium, the method comprising mixing a flowable dry powder composition comprising a mixture of diphenylcarbazide particles and glass bubbles, with a buffer solution to form a detection mixture; and, exposing the detection mixture to a sample potentially containing hexavalent chromium.

These and other aspects of the invention will be apparent from the detailed description below. In no event, however, should the above summaries be construed as limitations on the claimed subject matter, which subject matter is defined solely by the attached claims, as may be amended during prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", "bottom", "upper", "lower", "under", "over", "front", "back", "outward", "inward", "up" and "down", and "first" and "second" may be used in this disclosure, it should be understood that those terms are used in their relative sense only unless otherwise noted.

DETAILED DESCRIPTION

Figure 1:
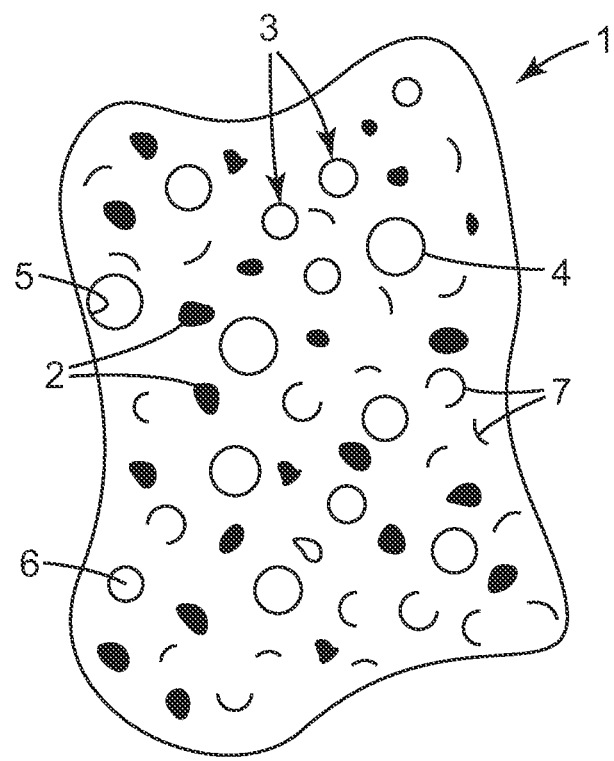
FIG. 1 is a view of an exemplary flowable dry powder composition as disclosed herein.

Shown in FIG. 1 is a flowable dry powder composition 1, comprising a mixture of diphenylcarbazide particles 2, and glass bubbles 3. Diphenylcarbazide (CAS number 140-22-7; also known by IUPAC name 1,3-bis(anilino)urea) is an indicator that is often used in the colorimetric detection of hexavalent chromium. For such purposes, diphenylcarbazide may be used in combination with a buffer solution in which the diphenylcarbazide is at least partially dissolved at an acidic pH conducive to the detection of hexavalent chromium. Thus, diphenylcarbazide may be conveniently packaged as a dry powder, along with a buffer solution with which it may be combined when it is desired to test a sample for the presence of hexavalent chromium.

By "dry powder" is meant that the particles (e.g., diphenylcarbazide and/or glass bubbles) are in the form of a conventional powder rather than as a dispersion, suspension, paste, etc. in a liquid; the term dry does not imply that the particles must be completely free of e.g. trace amounts of moisture etc. as may be typically present in most powders. By "flowable" is meant that dry powder composition 1 can satisfactorily flow through an e.g. 2 mm diameter orifice; the term does not encompass e.g. diphenylcarbazide particles and glass bubbles embedded within a solid matrix.

The inventor has found that, as a dry powder, diphenylcarbazide is slightly sticky and as such is difficult to process in mechanized filling equipment as are typically used to deposit powders into containers. In particular, the depositing of diphenylcarbazide into a fairly small container as may be used in a swab as described later herein, may involve flowing the diphenylcarbazide particles through an orifice, funnel, etc., with a diameter in the range of a few millimeters (e.g., 0.5-4 mm). It has been found that neat diphenylcarbazide is difficult to process through such equipment.

Numerous potentially suitable particulate flow agents have been examined for their ability to improve the flow properties of diphenylcarbazide particles without interfering with the ability of the diphenylcarbazide to perform satisfactorily as a hexavalent chromium indicator. It has been discovered that many particulate flow agents exhibit the drawback that, when the diphenylcarbazide is combined with a buffer solution in the presence of the flow agent, the diphenylcarbazide solution exhibits a noticeable color that unacceptably interferes with the ability of the diphenylcarbazide to display a colorimetric change in the presence of hexavalent chromium (diphenylcarbazide typically turns a pink-violet color in the presence of sufficient hexavalent chromium). Other materials, while not causing an interfering color, have not provided any improvement in flow properties.

Materials potentially useful as particulate flow agents but which have been found to unacceptably cause unwanted coloration of a diphenylcarbazide solution include e.g.: starch, sugar, sucrose, mannitol, lactose, polyester, phenolic microballoons, talc, sodium chloride, alumina, silica, and controlled pore glass. Materials potentially useful as particulate flow agents but which (even though they did not unacceptably cause unwanted coloration of a diphenylcarbazide solution) did not improve the flow properties of the diphenylcarbazide particles include e.g. expandable or expanded polymeric microballoons (e.g., of the type available from AkzoNobel, of Sundsvall, Sweden, under the trade designation EXPANCEL 461 DE).

Surprisingly, glass bubbles 3 have been found to serve as particulate flow agents that can improve the flow properties of diphenylcarbazide (such that a glass microsphere/diphenylcarbazide dry powder mixture can be satisfactorily processed in mechanized powder-handling and container-filling equipment), without causing an appreciable color to develop in a diphenylcarbazide solution.

Glass bubbles 3 can be of any suitable size (e.g., diameter, or equivalent diameter, since they need not be perfectly spherical). In various embodiments, they may range in size from about 0.2 microns to about 500 microns. In further embodiments, they may range in size from about 2 microns to about 100 microns. In specific embodiments, they may comprise a $50^{th}$% size of from about 30 microns to about 65 microns. They may be made of any suitable glass composition (e.g., silicate, aluminosilicate, soda-lime, borosilicate, soda-lime borosilicate, sodium silicate, and so on, noting that some overlap between the various listed compositions may exist).

Glass bubbles are hollow and can be produced e.g. by reducing (e.g., by milling) glass to a fine particle size, and heating the glass particles to a temperature in which surface tension causes the particle to assume a spherical shape and in which the high temperature also causes a latent blowing agent in the glass to decompose to form a gas which causes the glass particle to expand to take on a hollow generically spherical shape. Further details of exemplary glass bubbles and methods of making are found e.g. in U.S. Pat. No. 4,767,726 to Marshall. Glass bubbles comprise outer surface 4, and inner surface 5, which may surround interior hollow 6, all as illustrated in exemplary manner in FIG. 1.

Glass bubbles 3 are defined herein as being made of nonporous glass. The ordinary artisan will appreciate that glass bubbles are typically non-porous as conventionally made, meaning that they comprise generally solid outer surfaces 4 and inner surfaces 5 and have little or no detectable pore volume (hollow interior space 6 not being considered a pore volume in this context). They are thus contrasted from e.g. controlled-pore glass and from other porous inorganic materials (such as porous alumina, porous silica, etc.) and the like. In some embodiments, glass bubbles 3 may comprise a true density (which will be distinguished from bulk density) of from about 0.1 g/cc to about 0.6 g/cc. In further embodiments, glass bubbles 3 may comprise a true density of from about 0.15 g/cc to about 0.30 g/cc.

In various embodiments, glass bubbles 3 may comprise an oil absorption (as measured e.g. per ASTM D281-84) in the range of about 0.2-0.6 grams oil per cc of glass bubbles. In various embodiments, glass bubbles 3, when mixed into deionized water at approximately 5 volume percent, may provide a pH in the range of about 9.1-9.9. In some embodiments, glass bubbles 3 do not comprise any type of organic surface coating their outer surface. In other embodiments, they may comprise e.g. coupling agents and the like at least on their outer surface.

Suitable glass bubbles 3 may include e.g. those products available from 3M Company, St. Paul, Minn. under the trade designation 3M GLASS BUBBLES; for example those available under the designation General Purpose Series, K Series, S Series, HGS Series, Floated Series, and the like. Exemplary grades of glass bubbles which have been found to be particularly suitable are General Purpose K-20 and General Purpose K-1 grades available from 3M Company. Other potentially suitable glass bubbles (encompassing both solid and hollow microspheres) may include those available from Potters Industries, Valley Forge, Pa., under the trade designations QCEL, Z-CEL, SPHERICEL, SPHERIGLASS, TECHNICAL QUALITY A-SERIES, MEDISPHERE, and the like.

Glass bubbles 3 may be combined with the diphenylcarbazide particles in any suitable amount. In various embodiments, diphenylcarbazide may comprise from about 10 wt. % to about 90 wt. % of the total weight (of the combined diphenylcarbazide and glass bubbles), with the glass bubbles then comprising e.g. from about 90 wt. % to about 10 wt. % of the total combined weight. In further embodiments, the diphenylcarbazide may comprise from about 25 wt. % to about 50 wt. %, from about 50 wt. % to about 70 wt. %, or from about 70% to about 90% of the total combined weight. In particular embodiments e.g. for use with certain process equipment, a ratio in the range of about 17-23 wt. % K-1 glass bubbles to about 77-83 wt. % diphenylcarbazide may be optimal. In some embodiments, any suitable agent, additive, etc., may be present in flowable dry powder composition 1, for any purpose, as long as it does not unacceptably cause the above-discussed unwanted coloration, or cause any other unacceptable result. For example, some commercially available glass bubbles may contain a small amount (e.g., less than about 3 wt. %) of a synthetic silica additive as supplied by the glass bubble vendor. In some embodiments, the dry powder composition may consist essentially of a mixture of diphenylcarbazide particles 2 and glass bubbles 3 (such a condition does not preclude the presence e.g. of additives such as synthetic silica that may be present in some glass bubble products as supplied by the manufacturer). In some embodiments, the dry powder composition may consist of a mixture of diphenylcarbazide particles 2 and glass bubbles 3.

In some embodiments substantially all of glass bubbles 3 are in the form of unbroken spheres. (In this context, substantially all does not preclude the presence of some low level, e.g. 5 wt. % or less, of broken or fragmentary glass shards, as may typically be present in glass bubbles as conventionally manufactured and handled.) In some embodiments, a significant portion, e.g. from about 10% of the total weight of the glass bubbles, to about 80% of the total weight of the glass bubbles, may be in the form of broken shards 7, as shown in exemplary manner in FIG. 1. In this context, it is noted that the term glass bubbles, encompasses not merely (e.g., spherical) glass bubbles e.g. as originally made, but also shards and fragments derived therefrom. Glass bubbles 3 may be processed (e.g., either during the process of mixing them with diphenylcarbazide particles 2, or before or after this), to crush or shatter a desired percentage of the glass bubbles into shards.

Figure 2:
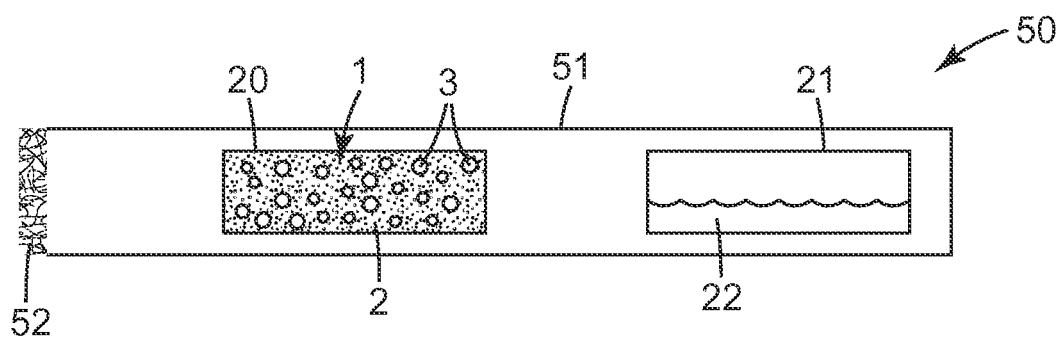
FIG. 2 is a side schematic cross sectional view of a swab comprising the flowable dry powder composition of FIG. 1.

Dry powder composition 1 comprising diphenylcarbazide particles 2, and glass bubbles 3, may be provided (e.g., to an end user) in a container 20, as shown in FIG. 2, which process may be performed e.g. by the use of mechanized powder-filling equipment, facilitated by the glass bubbles acting as a flow agent, as described above. Container 20 (with composition 1 therein) may be a breakable container (e.g., may be a sealed ampoule made of glass with walls of suitable thickness) by which is meant that container 20 is breakable by hand by a user (e.g., by squeezing container 20) without requiring any special equipment. Container 20 may be packaged in a secondary container 51 which may contain buffer solution 22. (Buffer solution 22 may conveniently contain e.g. water, acetone, ethanol, phosphoric acid, etc., and while referred to herein a solution for convenience, may contain any desired insoluble components as desired). In some embodiments, buffer solution 22 may be provided in a buffer container 21

(which may e.g. be a sealed container) within secondary container 51, as shown in exemplary manner in FIG. 2. Secondary container 51 may comprise walls which are made of a pliable material of appropriate thickness such that a user may manually squeeze or bend secondary container 51 a first time and/or in a first location to break container 20 containing dry powder mixture 1, and may manually squeeze or bend secondary container 51 a second time and/or in a second location to break container 21 containing buffer solution 22. Dry powder mixture 1 and buffer solution 22, having thus been liberated from their respective containers 20 and 21, may then be mixed with each other within secondary container 51 to form a detection mixture. (It is convenient to package dry powder mixture 1, and buffer solution 22 separately in this type of binary packaging system, because diphenylcarbazide eventually decomposes if left in solution for extended periods of time). The detection mixture may be brought into contact with a sample potentially containing hexavalent chromium, and may be optically interrogated, which term encompasses any process from visual inspection by a user, to the use of instrumentation.

Secondary container 51 may contain an open end (by which is merely meant an end that is not hermetically sealed) comprising a liquid-permeable porous member 52 through which the buffer/diphenylcarbazide solution may pass in order to be brought into contact with a sample. (It is noted that liquid-permeable member 52 may prevent some portion of the glass bubbles 3 from passing therethrough, or may allow substantially all of them to pass through, which may be of little consequence since glass bubbles 3 are typically not found to unacceptably interfere with the performance of the diphenylcarbazide, as explained herein.)

In summary, secondary container 51, liquid-permeable member 52 (which may be any suitable fibrous material, nonwoven, or the like), and containers 20 and 21 may collectively comprise swab 50, as illustrated in exemplary manner in FIG. 2, which may be used to test a sample for the presence of hexavalent chromium. (Swab 50 may be provided in a protective sleeve, e.g. a paper sleeve, if desired.) Further details of swabs and associated delivery systems of this general type are described in more detail in U.S. Pat. No. 5,039,618 to Stone, which is incorporated by reference herein. It must be emphasized however that there are many possible ways in which dry powder composition 1, comprising a mixture of diphenylcarbazide particles 2 and glass bubbles 3, may be provided or packaged, and the inventions disclosed herein are specifically not limited merely to delivery systems of the type exemplified by swab 50.

LIST OF EXEMPLARY EMBODIMENTS

Embodiment 1

A flowable dry powder composition comprising a mixture of diphenylcarbazide particles and glass bubbles.

Embodiment 2

The composition of embodiment 1 wherein at least some of the glass bubbles are in the form of broken shards.

Embodiment 3

The composition of embodiment 2 wherein at least about 10% of the glass bubbles, by weight, are in the form of broken shards.

Embodiment 4

The composition of any of embodiments 1-3 wherein the glass bubbles are made of soda-lime borosilicate glass.

Embodiment 5

The composition of any of embodiments 1-4 wherein the glass bubbles comprise a $50^{th}$ percentile particle size in the range of about 30 microns to about 65 microns.

Embodiment 6

The composition of any of embodiments 1-5 wherein the glass bubbles comprise an oil absorption of from about 0.2-0.6 grams oil per cc of glass bubbles.

Embodiment 7

The composition of any of embodiments 1-6 wherein the glass bubbles comprise a true density of from about 0.1 g/cc to about 0.3 g/cc.

Embodiment 8

The composition of any of embodiments 1-7 wherein the composition consists essentially of a mixture of diphenylcarbazide particles and glass bubbles.

Embodiment 9

The composition of any of embodiments 1-7 wherein the composition consists of a mixture of diphenylcarbazide particles and glass bubbles.

Embodiment 10

The composition of any of embodiments 1-9 wherein the composition is inside a sealed container.

Embodiment 11

The composition of embodiment 10 wherein the sealed container is a breakable container.

Embodiment 12

The composition of embodiment 11 wherein the breakable sealed container is within a secondary container.

Embodiment 13

The composition of embodiment 12 wherein the secondary container additionally contains a buffer solution.

Embodiment 14

A kit for detecting hexavalent chromium, comprising at least one disposable swab comprising a secondary container that contains: a breakable container containing a flowable dry powder composition comprising a mixture of diphenylcarbazide particles and glass bubbles, and, a buffer solution.

Embodiment 15

The kit of embodiment 14 wherein the breakable container is a sealed breakable container and wherein the secondary container further comprises a breakable buffer solution container, that contains the buffer solution.

Embodiment 16

The kit of any of embodiments 14-15 wherein the secondary container comprises an open end comprising a liquid-permeable porous member.

Embodiment 17

The kit of any of embodiments 14-15 comprising the flowable dry powder composition of any of embodiments 2-9.

Embodiment 18

A method of filling a container with a flowable dry powder composition, the method comprising flowing a flowable dry powder composition comprising a mixture of diphenylcarbazide particles and glass bubbles into the container.

Embodiment 19

The method of embodiment 18 further comprising the step of packaging the container within a secondary container that also contains a buffer solution.

Embodiment 20

The method of any of embodiments 18-19 wherein the flowable dry powder composition is the flowable dry powder composition of any of embodiments 2-9.

Embodiment 21

A method of detecting hexavalent chromium, the method comprising: mixing a flowable dry powder composition comprising a mixture of diphenylcarbazide particles and glass bubbles, with a buffer solution to form a detection mixture; and, exposing the detection mixture to a sample potentially containing hexavalent chromium.

Embodiment 22

The method of embodiment 21 further comprising the step of optically interrogating the detection mixture.

Embodiment 23

The method of any of embodiments 21-22 wherein the flowable dry powder composition is the flowable dry powder composition of any of embodiments 2-13.

EXAMPLES

Hexavalent Chromium Solution

A very small crystal of potassium dichromate was dissolved in approximately 5 cc of water in a glass vial. An orange solution was obtained.

Buffer Solution

Buffer solution was prepared by combining approximately 17.5 cc of acetone, approximately 17.5 cc of 95% aqueous ethanol, 20 cc of phosphoric acid 85%, and approximately 45 cc of deionized water in an 8 ounce glass jar. The jar was agitated until the ingredients were thoroughly mixed.

REPRESENTATIVE EXAMPLE

Dry Powder Mixture

Approximately 10 g of diphenylcarbazide (obtained from K&K Laboratories, of Plainview, N.Y.) was ground to fine powder using a mortar and pestle. Approximately 8 g of K20 GLASS BUBBLES from 3M Company, St. Paul Minn., was placed into a paper cup. 2 g of the ground diphenylcarbazide was added to the paper cup and the contents were then agitated by hand using a wooden tongue depressor until the faint yellow color of the diphenylcarbazide particles was dispersed homogeneously throughout the glass bubbles. Thus was produced a dry powder mixture containing approximately 20 wt. % diphenylcarbazide. A similar dry powder mixture was produced containing approximately 50 wt. % diphenylcarbazide.

Mixing of Dry Powder Mixture with Buffer Solution

To two glass vials were added approximately 25 mg each of the diphenylcarbazide-glass bubble dry powder mixture. Into each vial, approximately 0.5 cc of the buffer solution was added. The vials were then agitated and solution-dispersions (since the glass bubbles did not dissolve) best described as colorless were obtained.

Exposure of the Dry Powder/Buffer Solution-Dispersions to Hexavalent Chromium

A small drop of the above hexavalent chromium solution was deposited into each of two plastic weighing boats. To one weighing boat was added one drop of the 20 wt. % diphenylcarbazide/glass bubble solution-dispersion; to the other weighing boat was added one drop of the 50 wt. % diphenylcarbazide/glass bubble solution-dispersion. An intense purple color was immediately obtained in both cases, indicating satisfactory colorimetric indication of the presence of chromium.

Flow Properties of Dry Powder Mixture

Static mixing tips were obtained from Sulzer Chemtech, Winterthur, Switzerland and were modified to simulate the flow characteristics of a mechanized (e.g., automated) powder filler. The two powder mixtures (20 wt. % diphenylcarbazide and 50 wt. % diphenylcarbazide) were passed through these modified static mixers, and were considered to have satisfactory flow characteristics to allow their use in conventional mechanized powder filling equipment.

Variations

Glass bubbles were obtained from 3M Company, under the trade designations A20/1000 and H20/1000. The A20/1000 glass bubbles were listed by the vendor as having a methacrylato chromic chloride surface treatment; the H20/1000 glass bubbles were listed as having an epoxy silane surface treatment. Upon mixing the glass bubbles (in separate experiments) with diphenylcarbazide dye particles to make a dry powder composition in similar manner as described above for the Representative Example, satisfactory flow characteristics were obtained. Upon mixing the dry powder compositions with buffer solution, no detectable color was obtained. Upon exposure of the powder/buffer mixtures to hexavalent chromium, an intense purple color was immediately obtained, indicating satisfactory colorimetric indication of the presence of chromium.

Glass bubbles were obtained from Potters Industries, Valley Forge, Pa., under the trade designations QCEL and 7035, and were mixed with diphenylcarbazide dye particles to make a dry powder composition, in similar manner as described above for the Representative Example. Satisfactory flow characteristics were obtained. A slight color was obtained upon mixing the dry powder composition with the buffer solution; however, it was judged that the slight color did not unacceptably interfere with the ability to provide colorimetric indication of the presence of chromium.

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather extends at least to the structures described by the language of the claims, and the equivalents of those structures. To the extent that there is a conflict or discrepancy between this specification as written and the disclosure in any document incorporated by reference herein, this specification as written will control.

What is claimed is:

1. A flowable dry powder composition comprising a mixture of diphenylcarbazide particles and hollow glass bubbles wherein at least 5% of the glass bubbles by weight are in the form of broken shards.

2. The composition of claim 1 wherein the glass bubbles are made of soda-lime borosilicate glass.

3. The composition of claim 1 wherein the glass bubbles comprise a $50^{th}$ percentile particle size in the range of about 30 microns to about 65 microns.

4. The composition of claim 1 wherein the glass bubbles comprise an oil absorption of from about 0.2-0.6 grams oil per cc of glass bubbles.

5. The composition of claim 1 wherein the glass bubbles comprise a true density of from about 0.1 g/cc to about 0.3 g/cc.

6. The composition of claim 1 wherein the composition consists essentially of a mixture of diphenylcarbazide particles and glass bubbles.

7. The composition of claim 1 wherein the composition consists of a mixture of diphenylcarbazide particles and glass bubbles.

8. The composition of claim 1 wherein the composition is inside a sealed container.

9. The composition of claim 8 wherein the sealed container is a breakable container.

10. The composition of claim 9 wherein the breakable sealed container is within a secondary container.

11. The composition of claim 10 wherein the secondary container additionally contains a buffer solution.

12. A kit for detecting hexavalent chromium, comprising:
at least one disposable swab comprising a secondary container that contains:
a breakable container containing a flowable dry powder composition comprising a mixture of diphenylcarbazide particles and hollow glass bubbles wherein at least 5% of the glass bubbles by weight are in the form of broken shards,
and,
a buffer solution.

13. The kit of claim 12 wherein the breakable container is a sealed breakable container and wherein the secondary container further comprises a breakable buffer solution container, that contains the buffer solution.

14. The kit of claim 12 wherein the secondary container comprises an open end comprising a liquid-permeable porous member.

15. A method of filling a container with a flowable dry powder composition, the method comprising flowing the flowable dry powder composition of claim 1 into the container.

16. The method of claim 15 further comprising the step of packaging the container within a secondary container that also contains a buffer solution.

17. A method of detecting hexavalent chromium, the method comprising:
mixing the flowable dry powder composition of claim 1, with a buffer solution to form a detection mixture;
and,
exposing the detection mixture to a sample potentially containing hexavalent chromium.

18. The method of claim 17 further comprising the step of optically interrogating the detection mixture.

* * * * *